United States Patent
Wang et al.

(10) Patent No.: US 11,529,305 B2
(45) Date of Patent: Dec. 20, 2022

(54) SCRUB SPONGE AND PREPARATION METHOD THEREFOR

(71) Applicant: WUHAN BEBEVISA BIOTECH CO., LTD, Wuhan (CN)

(72) Inventors: Xiaojun Wang, Wuhan (CN); Huaixin Chen, Wuhan (CN); Qisheng Pan, Wuhan (CN)

(73) Assignee: WUHAN BEBEVISA BIOTECH CO., LTD, Wuhan (CN)

( * ) Notice: Subject to any disclaimer, the term of this patent is extended or adjusted under 35 U.S.C. 154(b) by 428 days.

(21) Appl. No.: 16/720,616

(22) Filed: Dec. 19, 2019

(65) Prior Publication Data

US 2020/0138698 A1   May 7, 2020

Related U.S. Application Data

(63) Continuation of application No. PCT/CN2018/082707, filed on Apr. 11, 2018.

(30) Foreign Application Priority Data

Sep. 8, 2017 (CN) .......................... 201710821298.6

(51) Int. Cl.
  *A61K 8/9794*    (2017.01)
  *A61K 8/02*     (2006.01)
  (Continued)

(52) U.S. Cl.
  CPC .......... *A61K 8/9794* (2017.08); *A61K 8/0279* (2013.01); *A61K 8/9789* (2017.08); *A61Q 19/10* (2013.01); *B29B 7/90* (2013.01); *B29B 11/16* (2013.01); *B29C 35/16* (2013.01); *A61K 2800/28* (2013.01); *B29K 2001/00* (2013.01); *B29K 2105/16* (2013.01); *B29L 2031/7406* (2013.01)

(58) Field of Classification Search
  None
  See application file for complete search history.

(56) References Cited

U.S. PATENT DOCUMENTS

2003/0045592 A1   3/2003   Shaw et al.
2016/0287029 A1   10/2016  Kim

FOREIGN PATENT DOCUMENTS

CN      101816525 A      9/2010
CN      101423613 B      2/2011
(Continued)

OTHER PUBLICATIONS

EPO English translation of CN107778543A (Year: 2018).*
(Continued)

*Primary Examiner* — Kyung S Chang
(74) *Attorney, Agent, or Firm* — Westbridge IP LLC

(57) ABSTRACT

Disclosed are a scrub sponge and a preparation method therefor. The method for preparing the scrub sponge includes the operations of: obtaining a first mixture by stirring alkalizer, porogen, konjac powder, scrub granule and water, and filling the first mixture into a mold to form a preform, where the preform includes a first sponge layer; forming a parison by sequentially cooking and freezing the preform; and sequentially unfreezing, dehydrating and drying the parison to obtain the scrub sponge.

5 Claims, 2 Drawing Sheets

(51) Int. Cl.
*A61K 8/9789* (2017.01)
*A61Q 19/10* (2006.01)
*B29B 7/90* (2006.01)
*B29B 11/16* (2006.01)
*B29C 35/16* (2006.01)
*B29K 1/00* (2006.01)
*B29K 105/16* (2006.01)
*B29L 31/00* (2006.01)

(56) References Cited

FOREIGN PATENT DOCUMENTS

| | | |
|---|---|---|
| CN | 102552051 A | 7/2012 |
| CN | 103214697 A | 7/2013 |
| CN | 103418020 A | 12/2013 |
| CN | 103462816 A | 12/2013 |
| CN | 106137824 A | 11/2016 |
| CN | 107625651 A | 1/2018 |
| CN | 107672243 A | 2/2018 |
| CN | 107778543 A * | 3/2018 |
| KR | 101118453 B1 | 2/2012 |
| WO | 2019068296 A1 | 4/2019 |

OTHER PUBLICATIONS

First Office Action in counterpart Chinese Application 201710821298. 6, dated Jun. 14, 2018.
International Search Report in corresponding international application No. PCT/CN2018/082707, dated Jun. 27, 2018.
Third Office Action in counterpart Chinese Application 201710821298. 6, dated Nov. 13, 2018.
Written Opinion in corresponding international application No. PCT/CN2018/082707, dated Jun. 27, 2018.
Extended European Search Report issued in counterpart European Patent Application No. 18853388.9, dated May 26, 2021.

* cited by examiner

SCRUB SPONGE AND PREPARATION METHOD THEREFOR

CROSS REFERENCE TO RELATED APPLICATIONS

The present application is a Continuation Application of International Application No. PCT/CN2018/082707, filed Apr. 11, 2018, which claims priority to Chinese Patent Application No. 201710821298.6, filed Sep. 8, 2017, the entire contents of which are hereby incorporated by reference.

FIELD

The present disclosure relates to the technical field of sponge preparation, and in particular to a scrub sponge and a preparation method therefor.

BACKGROUND

In general, existing exfoliators incorporate scrub granule in paste, cream or lotion, and when the skin is cleaned using such exfoliators, the exfoliation effect is achieved by the friction between the scrub granule and the skin. After use, moisturizing water, milk and other products are needed for moisturizing. The process is cumbersome and inconvenient. Moreover, the existing exfoliators generally contain a large amount of chemical components. Although the exfoliating cleaning effect is good, it is irritating to the skin, and long-term use may cause the stratum corneum to be too thin to damage the skin or make the skin sensitive.

SUMMARY

The main purpose of the present application is to provide a scrub sponge and a preparation method therefor, aiming at making the sponge have both exfoliation and moisturizing effects.

In order to achieve the above purpose, the present disclosure provides a scrub sponge including konjac sponge; and scrub granule uniformly embedded in the konjac sponge, where the scrub granule is natural plant granule.

Optionally, the konjac sponge includes a first sponge layer evenly embedded with the scrub granule; and a second sponge layer.

Optionally, the natural plant granule includes one or more components selected from apricot kernels granule, grape seeds granule and walnut seeds granule; where the natural plant granule has a grain size of 80 to 200 mesh.

The present disclosure further provides a method for preparing a scrub sponge including the following operations:
 forming a preform by stirring a mixture of alkalizer, porogen, konjac powder, scrub granule and water, and filling the mixture into a mold;
 forming a parison by sequentially cooking and freezing the preform; and,
 sequentially unfreezing, dehydrating and drying the parison.

Optionally, after obtaining a first mixture by stirring alkalizer, porogen, konjac powder, scrub granule and water, and filling the first mixture into a mold to form a preform, where the preform includes a first sponge layer, and before forming a parison by sequentially cooking and freezing the preform, the method further includes:
 obtaining a second mixture by stirring alkalizer, porogen, konjac powder and water, and filling the second mixture into the mold; and
 bonding the second sponge layer on the first sponge layer to form the preform.

Optionally, the konjac powder has an amount of glucomannan of at least 80%.

Optionally, the konjac powder is in an amount of 3% to 15% w/w, and water is in an amount of 85% to 97% w/w; where the alkalizer is in an amount of 0.3% to 3% w/w of the konjac powder, and the porogen is in an amount of 0.5% to 4% w/w of the konjac powder, and the scrub granule is in an amount of 20% to 45% w/w of the konjac powder.

Optionally, the alkalizer includes one or more components selected from calcium hydroxide, calcium oxide, sodium hydroxide, sodium carbonate and sodium hydrogen carbonate; where the porogen includes one or more components selected from Tween 20, Tween 60 and Tween 80.

Optionally, in the operation forming a parison by sequentially cooking and freezing the preform: the cooking has a temperature of 100 to 105° C. and a duration of 2 to 3 hours, and where the freezing has a temperature of −20 to −30° C. and a duration of 3 to 5 days.

Optionally, in the operation sequentially unfreezing, dehydrating and drying the parison to obtain the scrub sponge, the drying of the parison is vacuum freeze drying, where the vacuum freeze drying has a vacuum degree of 1.3 to 10 Pa, a freezing temperature of −30 to −50° C. and a drying duration of 16 to 20 hours.

In the technical solution of the present disclosure, natural plant granule is added as scrub granule to the konjac fiber sponge to realize fusion between the solid scrub granule and the solid sponge. The konjac fiber has the bacteriostatic and hydrating effect, and the scrub granule has the exfoliation effect, so that the combination of the konjac fiber and the scrub granule makes the scrub sponge has the effects of exfoliation, massage, cleaning and moisturizing at the same time. In addition, the raw materials are natural botanical ingredients without any irritating substances, which are suitable for users of different skin types.

BRIEF DESCRIPTION OF THE DRAWINGS

In order to more clearly illustrate the embodiments of the present disclosure or the technical solutions in the prior art, the drawings to be used in the embodiments or the prior art description will be briefly described below. Obviously, the drawings in the following description are only certain embodiments of the present disclosure, and other drawings can be obtained according to the structures shown in the drawings without any creative work for those skilled in the art.

The implementation, functional features and advantages of the present disclosure will be further described with reference to the accompanying drawings.

DETAILED DESCRIPTION OF THE EMBODIMENTS

It can be understood that the specific embodiments described herein are merely illustrative of the present disclosure and are not intended to be limited.

Figure 1:
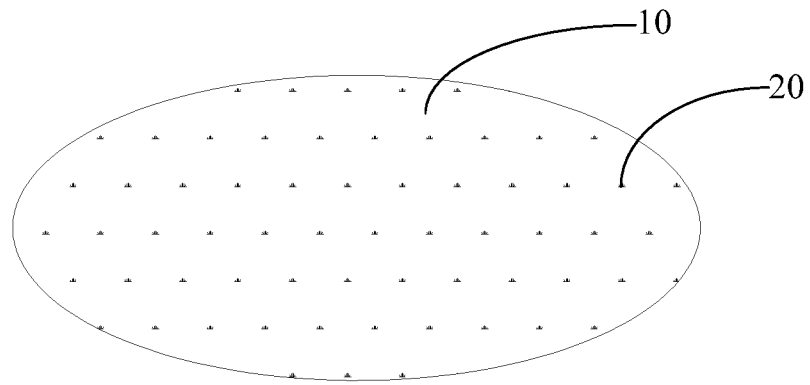
FIG. 1 is a schematic structural view of a scrub sponge according to an embodiment of the present disclosure.

The present disclosure provides a scrub sponge, and FIG. 1 is a scrub sponge according to an embodiment of the present disclosure. Referring to FIG. 1, the scrub sponge 100 includes konjac sponge 10 and scrub granule 20 uniformly embedded in the konjac sponge 10, where the scrub granule 20 is natural plant granule.

Since konjac is rich in glucomannan, and glucomannan has excellent cleansing and bacteriostatic properties and strong water absorption, the products prepared by konjac fiber have the dual functions of cleansing bacteriostatic and moisturizing. The scrub granule is added into the konjac powder to prepare a scrub sponge, which combines the exfoliating effect of the scrub granule with the cleansing bacteriostatic and moisturizing effects of the konjac fiber product, so that the scrub sponge has the effects of exfoliating, cleansing and moisturizing. In use, the exfoliation and moisturizing may be completed simultaneously by using the scrub sponge alone, without using moisturizing water, milk and other products for secondary care.

Figure 2:
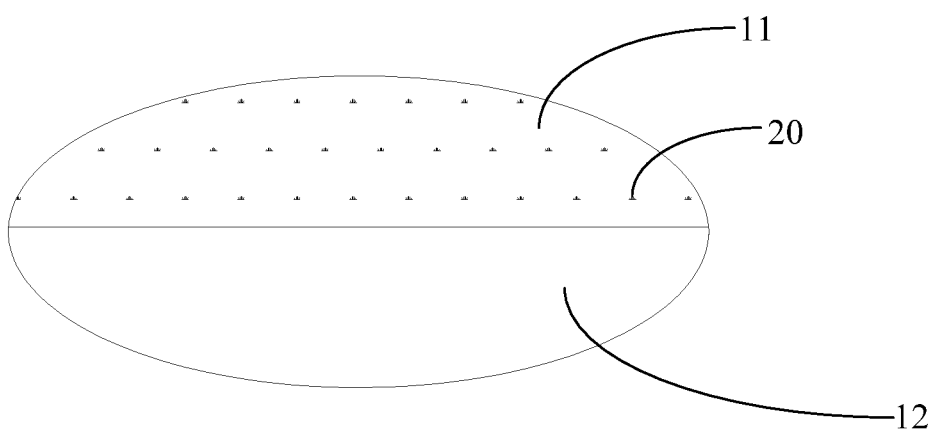
FIG. 2 is a schematic structural view of the scrub sponge according to another embodiment of the present disclosure.

In another embodiment of the scrub sponge provided by the present disclosure, referring to FIG. 2, the konjac sponge 100 includes a first sponge layer 11 evenly embedded with the scrub granule 20 and a second sponge layer 12.

For a scrub sponge containing scrub granule, the scrub granule may be uniformly dispersed throughout the konjac sponge, or a sponge having a two-layer structure may be obtained by controlling a molding process, where one layer is a first sponge layer firstly embedded with scrub granule, and the other layer is a second sponge layer that does not contain scrub granule. In the process of using the double-layered scrub sponge, the skin may be exfoliated and massaged through the first sponge layer, and then the skin is hydrated and moisturized through the second sponge layer.

Optionally, the natural plant granule includes one or more components selected from apricot kernels granule, grape seeds granule and walnut seeds granule. Exfoliation through the chemical composition is prone to cause skin allergies during use. The scrub granule used in the present disclosure is natural plant granule, which avoids skin sensitivity caused by chemical exfoliators.

Preferably, the natural plant granule has a grain size of 80 to 200 mesh. The grain size of the scrub granule is too large, so that the scrub sponge is too rough, and it is easy to damage the skin during use. Therefore, the scrub granule is sieved, the size of the mesh is 80 to 200 mesh, and the sieved scrub granule is used for preparing a scrub sponge, so that the scrub sponge may not be excessively rough and damage the skin.

Figure 3:
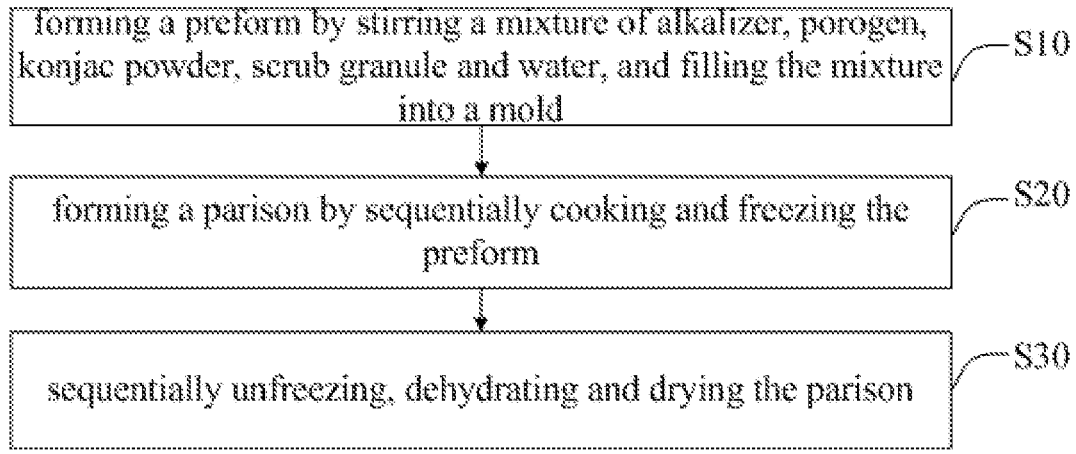
FIG. 3 is a schematic flow chart of a method for preparing a scrub sponge according to an embodiment of the present disclosure.

The present disclosure further provides a method for preparing a scrub sponge. FIG. 3 is an embodiment of a method for preparing a scrub sponge provided by the present disclosure. Referring to FIG. 1, the method for preparing the scrub sponge includes the following operations:

S10, forming a preform by stirring a mixture of alkalizer, porogen, konjac powder, scrub granule and water, and filling the mixture into a mold.

The alkalizer, the porogen, the konjac powder and the scrub granule are respectively weighed, and the alkalizer and the porogen are completely dissolved in water, and then the konjac powder and the scrub granule are added for stirring for 6 to 15 minutes, the mixture is in a semi-gel state and then filled into a mold to form a preform.

Optionally, the konjac powder is in an amount of 3% to 15% w/w, and water is in an amount of 85% to 97% w/w; and the alkalizer is in an amount of 0.3% to 3% w/w of the konjac powder, and the porogen is in an amount of 0.5% to 4% w/w of the konjac powder, and the scrub granule is in an amount of 20% to 45% w/w of the konjac powder.

S20, forming a parison by sequentially cooking and freezing the preform.

After the semi-gel state material is filled into the mold to form the preform, the preform is directly subjected to high-temperature cooking to form a fiber structure, and then subjected to freezing treatment to shrink the fiber structure to form a network porous structure, thereby obtaining a scrub sponge parison having a fine and dense porous structure.

Optionally, in the operation S20: the cooking has a temperature of 100 to 105° C. and a duration of 2 to 3 hours, and the freezing has a temperature of −20 to −30° C. and a duration of 3 to 5 days.

S30, sequentially unfreezing, dehydrating and drying the parison.

After the parison is unfrozen, a dehydration treatment is performed by a high-speed centrifuge to remove the moisture therein, and then the water is further removed by drying to obtain a scrub sponge. When the scrub sponge is used, it is first immersed in water. When the scrub sponge is swelled to restore elasticity, it may be used to clean the skin. After use, it may be hung in a ventilated and dry place to dry.

Optionally, in the operation S30, the drying of the parison is vacuum freeze drying, where the vacuum freeze drying has a vacuum degree of 1.3 to 10 Pa, a freezing temperature of −30 to −50° C. and a drying duration of 16 to 20 hours.

Figure 4:
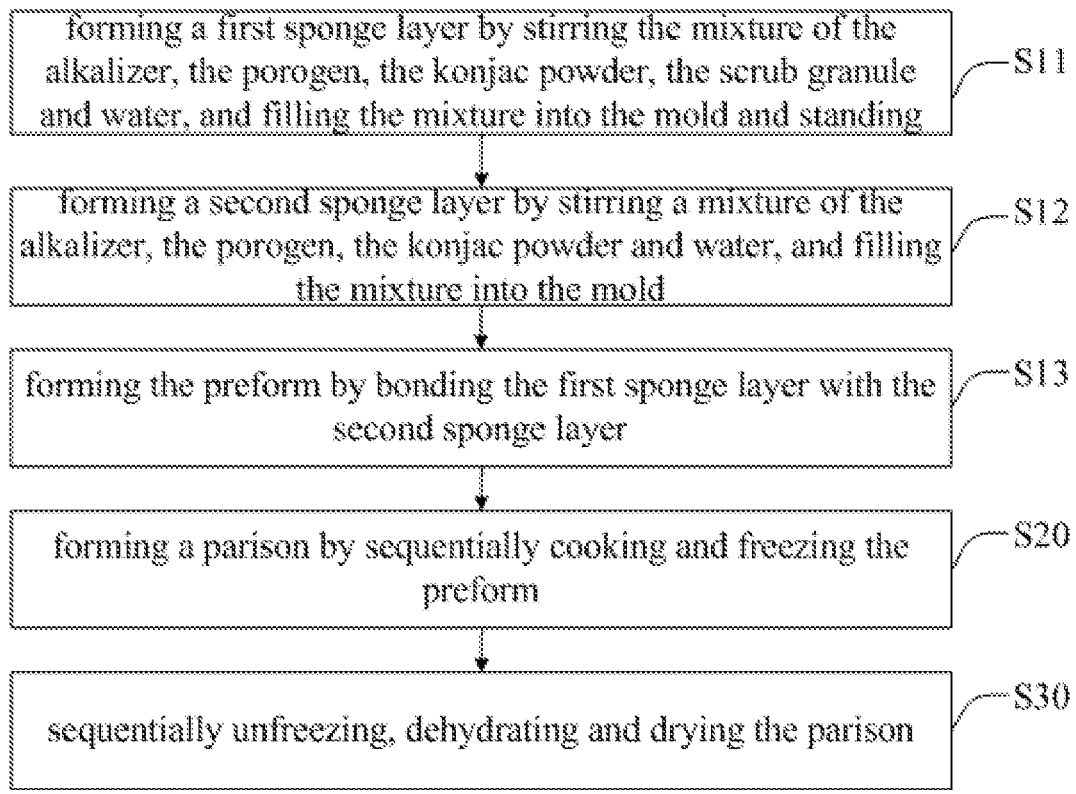
FIG. 4 is a schematic flow chart of the method for preparing the scrub sponge according to another embodiment of the present disclosure.

In another embodiment of the method for preparing the scrub sponge provided by the present disclosure, referring to FIG. 4, and operation S10 includes:

S11, forming a first sponge layer by stirring the mixture of the alkalizer, the porogen, the konjac powder, the scrub granule and water, and filling the mixture into the mold and standing.

For the two-layer structure of the scrub sponge, it may be prepared by controlling the molding process. Firstly, a first mixture formed by uniformly stirring the alkalizer, the porogen, the konjac powder, the scrub granule and water is filled into the mold, and left to stand for 20 to 40 minutes to form a first sponge layer, where the filling amount of the first mixture is 45 to 55% of the volume of the mold. Certainly, the filling amount of the first mixture may be determined according to the specific thickness requirement of the first sponge layer in the scrub sponge.

S12, forming a second sponge layer by stirring a mixture of the alkalizer, the porogen, the konjac powder and water, and filling the mixture into the mold.

A second mixture formed by uniformly stirring the alkalizer, the porogen, the konjac powder and water is filled into the mold in which the first sponge layer is formed, and is subjected to secondary molding to form a second sponge layer. Certainly, in the technical solution of the present disclosure, the sequence of the operation S11 and the operation S12 is not specifically limited herein, and the first sponge layer may be formed first, or the second sponge layer may be formed first. In other embodiments of the present disclosure, the first sponge layer and the second sponge layer may also be formed by two molds, respectively.

S13, forming the preform by bonding the first sponge layer with the second sponge layer.

Since the first sponge layer and the second sponge layer after molding are both gel-like substances, they are easily bonded together to form a preform having a two-layer structure.

Optionally, the konjac powder has an amount of glucomannan of at least 80%. As the main component of konjac powder, glucomannan has the functions of cleansing bacteriostatic and hydration moisturizing. If the content is too low, the strength of konjac fiber products may be insufficient, and the prepared sponge is easily deformed and damaged. The konjac powder with a content of not less than 80% of glucomannan is used as a main raw material to prepare a scrub sponge, so that the strength of the konjac fiber may be ensured, thereby improving the strength of the network of the multi-space structure in the scrub sponge, so that the scrub sponge may be used repeatedly without being deformed and damaged.

Optionally, the alkalizer includes one or more components selected from calcium hydroxide, calcium oxide, sodium hydroxide, sodium carbonate and sodium hydrogen carbonate; and the porogen includes one or more components selected from Tween 20, Tween 60 and Tween 80. The alkalizer mainly functions to provide a weakly alkaline environment, and neutralize the konjac powder mixed with water to form a small amount of acidic substances generated during the gel process. The addition of the porogen assists the preform to form a stable, dense pore-like fibrous structure during the cooking process. Tween is used as a recognized non-toxic, non-irritating material, and Tween added as the porogen may prevent the scrub sponge from irritating the skin during use.

In order to make the preparation process of the scrub sponge provided by the present disclosure more intuitive, the following application embodiments and comparative embodiments are explained:

Embodiment 1

(1) Forming a first sponge layer: weighing 3 g of sodium hydroxide, 5 g of Tween 20, 1000 g of konjac powder and 15000 g of purified water, respectively, dissolving sodium hydroxide and Tween in water, adding konjac powder and stirring for 10 min to obtain a first mixture, taking 30 g of the first mixture, filling the first mixture into a mold through a filling machine, and then standing for 20 min to form a first sponge layer;

(2) Forming a second sponge layer: weighing 3 g of sodium hydroxide, 5 g of Tween 20, 1000 g of konjac powder, 250 g of apricot kernels (80 mesh) and 15000 g of purified water, respectively, dissolving sodium hydroxide and Tween in water, adding konjac powder and stirring for 10 min, then adding apricot kernels and stirring for another 5 min to obtain a second mixture, taking 30 g of the second mixture, filling the second mixture into the mold formed with the first sponge layer through a filling machine to form a preform;

(3) Cooking and freezing: the obtained preform is subjected to gradient cooking, the cooking temperature is controlled from 100 to 105° C., and after cooking for 2 hours, it is cooled to normal temperature, and then it is placed in a cold storage for freezing treatment, and frozen at −20° C. for 3 days to obtain a parison;

(4) Dehydration and drying: After the parison is unfrozen, rinsed and trimmed, it is dehydrated by a high-speed centrifuge, and then vacuum-dried under an environment of a vacuum degree of 1.3 Pa and a temperature of −30° C. After drying for 20 hours, it is sealed and packaged to obtain a scrub sponge product.

Embodiment 2

(1) Forming a first sponge layer: weighing 20 g of ammonium hydrogen carbonate, 10 g of Tween 60, 1000 g of konjac powder and 15000 g of purified water, respectively, dissolving ammonium hydrogen and Tween in water, adding konjac powder and stirring for 10 min to obtain a first mixture, taking 30 g of the first mixture, filling the first mixture into a mold through a filling machine, and then standing for 30 min to form a first sponge layer;

(2) Forming a second sponge layer: weighing 20 g of ammonium hydrogen carbonate, 10 g of Tween 60, 1000 g of konjac powder, 250 g of apricot kernels (120 mesh) and 15000 g of purified water, respectively, dissolving ammonium hydrogen and Tween in water, adding konjac powder and stirring for 10 min, then adding apricot kernels and stirring for another 5 min to obtain a second mixture, taking 30 g of the second mixture, filling the second mixture into the mold formed with the first sponge layer through a filling machine to form a preform;

(3) Cooking and freezing: the obtained preform is subjected to gradient cooking, the cooking temperature is controlled from 100 to 105° C., and after cooking for 2 hours, it is cooled to normal temperature, and then it is placed in a cold storage for freezing treatment, and frozen at −25° C. for 4 days to obtain a parison;

(4) Dehydration and drying: After the parison is unfrozen, rinsed and trimmed, it is dehydrated by a high-speed centrifuge, and then vacuum-dried under an environment of a vacuum degree of 4 Pa and a temperature of −40° C. After drying for 18 hours, it is sealed and packaged to obtain a scrub sponge product.

Embodiment 3

(1) Forming a first sponge layer: weighing 30 g of calcium hydroxide, 25 g of Tween 60, 10 g of Tween 80, 1000 g of konjac powder and 15000 g of purified water, respectively, dissolving calcium hydroxide and Tween in water, adding konjac powder and stirring for 10 min to obtain a first mixture, taking 30 g of the first mixture, filling the first mixture into a mold through a filling machine, and then standing for 20 min to form a first sponge layer;

(2) Forming a second sponge layer: weighing 30 g of calcium hydroxide, 25 g of Tween 60, 10 g of Tween 80, 1000 g of konjac powder, 250 g of apricot kernels (200 mesh) and 15000 g of purified water, respectively, dissolving calcium hydroxide and Tween in water, adding konjac powder and stirring for 10 min, then adding apricot kernels and stirring for another 5 min to obtain a second mixture, taking 30 g of the second mixture, filling the second mixture into the mold formed with the first sponge layer through a filling machine to form a preform;

(3) Cooking and freezing: the obtained preform is subjected to gradient cooking, the cooking temperature is controlled from 100 to 105° C., and after cooking for 2 hours, it is cooled to normal temperature, and then it is placed in a cold storage for freezing treatment, and frozen at −20° C. for 5 days to obtain a parison;

(4) Dehydration and drying: After the parison is unfrozen, rinsed and trimmed, it is dehydrated by a high-speed centrifuge, and then vacuum-dried under an environment of a vacuum degree of 8 Pa and a temperature of −50° C. After drying for 16 hours, it is sealed and packaged to obtain a scrub sponge product.

Embodiment 4

(1) Forming a first sponge layer: weighing 20 g of sodium carbonate, 40 g of Tween 60, 1000 g of konjac powder and 15000 g of purified water, respectively, dissolving sodium carbonate and Tween in water, adding konjac powder and stirring for 10 min to obtain a first mixture, taking 30 g of the first mixture, filling the first mixture into a mold through a filling machine, and then standing for 20 min to form a first sponge layer;

(2) Forming a second sponge layer: weighing 20 g of sodium carbonate, 40 g of Tween 60, 1000 g of konjac powder, 300 g of grape seeds (120 mesh) and 15000 g of purified water, respectively, dissolving sodium carbonate and Tween in water, adding konjac powder and stirring for 10 min, then adding grape seeds and stirring for another 5 min to obtain a second mixture, taking 30 g of the second mixture, filling the second mixture into the mold formed with the first sponge layer through a filling machine to form a preform;

(3) Cooking and freezing: the obtained preform is subjected to gradient cooking, the cooking temperature is controlled from 100 to 105° C., and after cooking for 2 hours, it is cooled to normal temperature, and then it is placed in a cold storage for freezing treatment, and frozen at −30° C. for 4 days to obtain a parison;

(4) Dehydration and drying: After the parison is unfrozen, rinsed and trimmed, it is dehydrated by a high-speed centrifuge, and then vacuum-dried under an environment of a vacuum degree of 10 Pa and a temperature of −40° C. After drying for 16 hours, it is sealed and packaged to obtain a scrub sponge product.

The scrub sponge prepared by the above embodiments combines the exfoliation effect of the scrub granule with the cleansing and bacteriostatic effects of the konjac fiber products. Where the first sponge layer (with the scrub granule) of the scrub sponge has exfoliation, cleansing and skin care effects, and the second sponge layer of the scrub sponge (without scrub granule) has the hydration and moisturizing effects. During use, the exfoliation and moisturizing may be completed simultaneously without using moisturizing water, milk, etc for secondary care. The raw materials are natural botanical ingredients without any irritating substances, which are suitable for users of different skin types.

The above description refers to only optional embodiments of the present disclosure, and thus does not limit the scope of the present disclosure, and any transformation of equivalent structure made under the inventive concept of the present disclosure by using the contents of this specification and attached drawings, or direct/indirect application in other relevant technical fields, shall be included in the scope of the present disclosure.

What is claimed is:

1. A method for preparing a scrub sponge, the scrub sponge comprising a konjac sponge and a scrub granule uniformly embedded in the konjac sponge, the scrub granule being a natural plant granule with a grain size of 80 to 200 mesh, the method comprising the following operations:
   obtaining a first mixture by stirring alkalizer, porogen, konjac powder, scrub granule and water, and filling the first mixture into a mold to form a preform, wherein the preform comprises a first sponge layer;
   forming a parison by sequentially cooking and freezing the preform; and
   sequentially unfreezing, dehydrating and drying the parison to obtain the scrub sponge;
   wherein the konjac powder is in an amount of 3% to 15% w/w, and water is in an amount of 85% to 97% w/w; the alkalizer is in an amount of 0.3% to 3% w/w of the konjac powder, and the porogen is in an amount of 0.5% to 4% w/w of the konjac powder, and the scrub granule is in an amount of 20% to 45% w/w of the konjac powder;
   the alkalizer comprises one or more components selected from calcium hydroxide, calcium oxide, sodium hydroxide, sodium carbonate and sodium hydrogen carbonate; and
   wherein the porogen comprises one or more components selected from Tween 20, Tween 60 and Tween 80.

2. The method for preparing the scrub sponge of claim 1, wherein after obtaining the first mixture by stirring alkalizer, porogen, konjac powder, scrub granule and water, and filling the first mixture into a mold to form the preform, wherein the preform comprises the first sponge layer, and before forming the parison by sequentially cooking and freezing the preform, the method further comprises:
   forming a second sponge layer by stirring a second mixture of alkalizer, porogen, konjac powder and water, and filling the second mixture into the mold; and
   bonding the second sponge layer on the first sponge layer to form the preform.

3. The method for preparing the scrub sponge of claim 1, wherein the konjac powder has an amount of glucomannan of at least 80%.

4. The method for preparing the scrub sponge of claim 1, wherein in the operation forming the parison by sequentially cooking and freezing the preform:
   the cooking has a temperature of 100 to 105° C. and a duration of 2 to 3 hours, and
   wherein the freezing has a temperature of −20 to −30° C. and a duration of 3 to 5 days.

5. The method for preparing the scrub sponge of claim 1, wherein in the operation sequentially unfreezing, dehydrating and drying the parison to obtain the scrub sponge:
   the drying of the parison is vacuum freeze drying, wherein the vacuum freeze drying has a vacuum degree of 1.3 to 10 Pa, a freezing temperature of −30 to −50° C. and a drying duration of 16 to 20 hours.

* * * * *